US012433700B2

(12) United States Patent
Rockrohr

(10) Patent No.: US 12,433,700 B2
(45) **Date of Patent: *Oct. 7, 2025**

(54) ROBOTIC SURGICAL ASSEMBLIES

(71) Applicant: Covidien LP, Mansfield, MA (US)

(72) Inventor: Brian Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 354 days.

This patent is subject to a terminal disclaimer.

(21) Appl. No.: 18/140,818

(22) Filed: Apr. 28, 2023

(65) Prior Publication Data

US 2023/0320796 A1 Oct. 12, 2023

Related U.S. Application Data

(63) Continuation of application No. 17/013,936, filed on Sep. 8, 2020, now Pat. No. 11,666,395, which is a (Continued)

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02); *A61B 2034/302* (2016.02); *A61B 2034/305* (2016.02)

(58) Field of Classification Search
CPC ... A61B 17/068; A61B 17/28; A61B 17/2804; A61B 17/29; A61B 17/00234;
(Continued)

(56) References Cited

U.S. PATENT DOCUMENTS 6,132,368 A 10/2000 Cooper
6,206,903 B1 3/2001 Ramans
(Continued)

FOREIGN PATENT DOCUMENTS

JP 2011115594 A 6/2011
JP 2012235936 A 12/2012
(Continued)

OTHER PUBLICATIONS

Canadian Office Action issued in Canadian Patent Application No. 2,987,652 dated Sep. 6, 2023 (7 pages).
(Continued)

*Primary Examiner* — Dianne Dornbusch
(74) *Attorney, Agent, or Firm* — Carter, DeLuca & Farrell LLP

(57) ABSTRACT

A surgical instrument for use with and for selective connection to an instrument drive unit includes an end effector, an instrument drive connector including a plurality of drive assemblies, and a plurality of drive members in mechanical cooperation with the instrument drive connector and the end effector. Each drive assembly of the plurality of drive assemblies includes a drive screw including an elongated threaded body and a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

20 Claims, 13 Drawing Sheets

Related U.S. Application Data continuation of application No. 15/735,058, filed as application No. PCT/US2016/038367 on Jun. 20, 2016, now Pat. No. 10,779,897.

(60) Provisional application No. 62/183,363, filed on Jun. 23, 2015.

(58) Field of Classification Search
CPC .. A61B 2017/0046; A61B 2017/00464; A61B 2017/00473; A61B 2017/00367; A61B 2017/00477; A61B 34/30; A61B 34/71; A61B 34/32002; A61B 2034/302; A61B 2034/303; A61B 2034/305
See application file for complete search history.

(56) References Cited

U.S. PATENT DOCUMENTS 6,246,200 B1 6/2001 Blumenkranz et al.
6,312,435 B1 11/2001 Wallace et al.
6,331,181 B1 12/2001 Tierney et al.
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,793,812 B2 9/2010 Moore et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.

(56) References Cited

U.S. PATENT DOCUMENTS

| | | | |
|---|---|---|---|
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,420,620 | B2 | 9/2019 | Rockrohr |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,779,897 | B2 | 9/2020 | Rockrohr |

(56) References Cited

U.S. PATENT DOCUMENTS 10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs, II et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.
11,109,925 B2 9/2021 Cooper et al.
11,116,578 B2 9/2021 Hoffman et al.
11,129,683 B2 9/2021 Steger et al.
11,135,029 B2 10/2021 Suresh et al.
11,147,552 B2 10/2021 Burbank et al.
11,147,640 B2 10/2021 Jarc et al.
11,154,373 B2 10/2021 Abbott et al.
11,154,374 B2 10/2021 Hanuschik et al.
11,160,622 B2 11/2021 Goldberg et al.
11,160,625 B2 11/2021 Wixey et al.
11,161,243 B2 11/2021 Rabindran et al.
11,166,758 B2 11/2021 Mohr et al.
11,166,770 B2 11/2021 DiMaio et al.
11,166,773 B2 11/2021 Ragosta et al.
11,173,597 B2 11/2021 Rabindran et al.
11,185,378 B2 11/2021 Weir et al.
11,191,596 B2 12/2021 Thompson et al.
11,197,729 B2 12/2021 Thompson et al.
11,213,360 B2 1/2022 Hourtash et al.
11,221,863 B2 1/2022 Azizian et al.
11,234,700 B2 2/2022 Ragosta et al.
11,241,274 B2 2/2022 Vaders et al.
11,241,290 B2 2/2022 Waterbury et al.
11,259,870 B2 3/2022 DiMaio et al.
11,259,884 B2 3/2022 Burbank
11,272,993 B2 3/2022 Gomez et al.
11,272,994 B2 3/2022 Saraliev et al.
11,291,442 B2 4/2022 Wixey et al.
11,291,513 B2 4/2022 Manzo et al.
11,666,395 B2 6/2023 Rockrohr
2010/0331820 A1 12/2010 Prisco et al.
2011/0174099 A1 7/2011 Ross et al.
2012/0116416 A1 5/2012 Neff et al.
2012/0158013 A1 6/2012 Stefanchik et al.
2013/0041403 A1 2/2013 Cunningham et al.
2013/0282052 A1 10/2013 Aranyi et al.
2013/0319706 A1 12/2013 Nicholas et al.
2014/0005653 A1 1/2014 Shelton, IV et al.
2014/0252067 A1 9/2014 Moore et al.
2015/0080907 A1 3/2015 Herrell et al.
2016/0303743 A1 10/2016 Rockrohr

FOREIGN PATENT DOCUMENTS

JP 2012531943 A 12/2012
JP 6719487 B2 7/2020
KR 20110109475 A 10/2011
WO 2011016640 A2 2/2011
WO 2012112888 A2 8/2012
WO 2015088647 A1 6/2015

OTHER PUBLICATIONS

Chinese Office Acton dated Nov. 9, 2023 issued in Chinese Patent Application No. 2020112846223 (11 pages).
ISR Written Opinion of PCT/US2016/038367 dated Sep. 12, 2016.
Extended European Search Report corresponding to counterpart Patent Appln No. EP 16815110.8 dated Jan. 23, 2019.
Japanese Office Action dated Mar. 23, 2020 corresponding to counterpart Patent Application JP 2017-565916.
Chinese First Office Action dated Mar. 18, 2020 corresponding to counterpart Patent Application CN 201680036211.8.
Australian Examination Report No. 1 dated Feb. 13, 2020 corresponding to counterpart Patent Application AU 2016284040.
Indian Office Action dated Jun. 24, 2021 corresponding to counterpart Patent Application IN 201717045722.
Australian Examination Report No. 1 dated Jul. 8, 2021 corresponding to counterpart Patent Application AU 2020204226.

ROBOTIC SURGICAL ASSEMBLIES

CROSS-REFERENCE TO RELATED APPLICATIONS

This application is a continuation of U.S. patent application Ser. No. 17/013,936, filed Sep. 8, 2020, now U.S. Pat. No. 11,666,395, which is a continuation of U.S. patent application Ser. No. 15/735,058, filed Dec. 8, 2017, now U.S. Pat. No. 10,779,897, which is a National Stage application filed under 35 U.S.C. § 371 of International Patent Application Serial No. PCT/US2016/038367, filed Jun. 20, 2016, which claims the benefit of and priority to U.S. Provisional Patent Application Ser. No. 62/183,363, filed Jun. 23, 2015, the entire disclosure of each of which is incorporated by reference herein.

BACKGROUND

Robotic surgical systems have been used in minimally invasive medical procedures. Some robotic surgical systems included a console supporting a robot arm, and surgical instruments with different end effectors, such as forceps or a grasping tool, that were mounted to the robot arm via a wrist assembly. During a medical procedure, the end effector and the wrist assembly of the surgical instrument were inserted into a small incision (via a cannula) or a natural orifice of a patient to position the end effector at a work site within the body of the patient.

These surgical instruments had cables extending longitudinally from spools at a proximal end through an elongated shaft and the wrist assembly to the end effector. The cables were actuated by means of motors coupled to the spools when the surgical instrument was attached to the robot arm. The surgeon manipulated an input device of the robotic system and the robotic system actuated the motors to move the surgical instrument and end effector in a correlated manner.

The cables in the surgical instruments were prone to stretch during use. The stretching could cause end effector movement to lag that of the input device based on the amount of stretch. As a result, the surgical instrument and end effector may appear to move in a less correlated manner, which would limit the responsive performance of the robotic system.

There is a need to reduce cable stretch in robotic surgical instruments.

SUMMARY

In one aspect of the present disclosure, a surgical instrument for use with and for selective connection to an instrument drive unit includes an end effector defining a longitudinal axis, an instrument drive connector including a housing assembly and a plurality of drive assemblies at least partially disposed within the housing assembly, and a plurality of drive members in mechanical cooperation with the instrument drive connector and the end effector. Each drive assembly of the plurality of drive assemblies includes a drive screw including an elongated threaded body. The drive screw is rotatably supported within the housing assembly. The drive assembly also includes a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

Each drive screw of the plurality of drive assemblies may include a proximal end having an input drive coupler configured to receive rotational forces.

Each drive nut of the plurality of drive assemblies may include a first rail extending longitudinally along an outer surface thereof. The first rail may be slidingly disposed within a longitudinally extending channel formed within the housing assembly.

In some embodiments, the instrument drive connector includes a drive connector frame disposed within the housing assembly and in mechanical cooperation with the plurality of drive assemblies.

The drive connector frame may include a proximal end including a plurality of proximal bearings. Each bearing of the plurality of proximal bearings may be dimensioned to retain a proximal end of the drive screw of one of the plurality of drive assemblies.

The drive connector frame may include an elongated central shaft, and the plurality of proximal bearings may be disposed radially around the elongated central shaft.

The elongated central shaft may include a plurality of longitudinally extending grooves defined in an outer surface thereof. Each groove of the plurality of longitudinally extending grooves may be configured to slidingly receive a portion of a respective one of the plurality of drive members.

Each of the drive nuts of the plurality of drive assemblies may include a second rail extending longitudinally along an outer surface thereof. The second rail may be slidingly disposed within one of the plurality of longitudinally extending grooves of the elongated central shaft of the drive connector frame.

In some embodiments, each drive member includes a flexible distal end and a rigid proximal end. The proximal end may be secured to one of the drive nuts of the plurality of drive assemblies.

The plurality of drive members may include a first drive member and a second drive member, and the end effector may include first and second jaw members and first and second jaw pulleys. The first drive member may be engaged with the first jaw pulley and the second jaw member may be engaged with the second jaw pulley such that longitudinal translation of the first and/or second drive members yaws the first and second jaw members about a first pivot axis that is orthogonal to the longitudinal axis of the end effector and/or moves the first and/or second jaw members relative to each other.

The end effector may include a clevis pivotally mounted to a set of idler pulleys. The first and second jaw pulleys may be coupled to the clevis and the first and second drive members may be engaged with the set of idler pulleys such that longitudinal translation of the first and/or second drive members pitches the first and second jaw members about a second pivot axis that is orthogonal to both the first pivot axis and the longitudinal axis of the end effector.

In another aspect of the present disclosure, an instrument drive connector for selectively interconnecting a surgical instrument having an end effector that is configured to perform a function and an instrument drive unit that is configured to actuate the end effector, includes a housing assembly defining a bore, a plurality of drive assemblies at least partially disposed within the bore of the housing assembly, and a plurality of drive members in mechanical cooperation with the instrument drive connector and the end effector. Each drive assembly of the plurality of drive assemblies includes a drive screw including an elongated threaded body and is rotatably supported within the housing assembly, and a drive nut threadedly engaged with the elongated threaded body of the drive screw such that rotation of the drive screw results in longitudinal movement of the drive nut. Each drive member of the plurality of drive members includes a proximal end portion secured to a respective drive nut of one of the plurality of drive assemblies such that longitudinal translation of the respective drive nut causes longitudinal translation of the drive member to drive a function of the end effector.

Each drive screw of the plurality of drive assemblies may include a proximal end having an input drive coupler configured to engage the instrument drive unit and to receive rotational forces.

Each drive nut of the plurality of drive assemblies may include a first rail extending longitudinally along an outer surface thereof. The first rail may be slidingly disposed within a longitudinally extending channel formed in the bore of the housing assembly.

In some embodiments, the instrument drive connector includes a drive connector frame disposed within the bore of the housing assembly and in mechanical cooperation with the plurality of drive assemblies.

The drive connector frame may include a proximal end including a plurality of proximal bearings. Each bearing of the plurality of proximal bearings may be dimensioned to retain a proximal end of the drive screw of one of the plurality of drive assemblies.

The drive connector frame may include an elongated central shaft, and the plurality of proximal bearings may be disposed radially around the elongated central shaft.

The elongated central shaft may include a plurality of longitudinally extending grooves defined in an outer surface thereof. Each groove of the plurality of longitudinally extending grooves may be configured to slidingly engage a portion of a respective one of the plurality of drive members.

Each of the drive nuts of the plurality of drive assemblies may include a second rail extending longitudinally along an outer surface thereof. The second rail may be slidingly disposed within one of the plurality of longitudinally extending grooves of the elongated central shaft of the drive connector frame.

In some embodiments, each drive member includes a flexible distal end and a rigid proximal end. The proximal end may be secured to one of the drive nuts of the plurality of drive assemblies.

Other aspects, features, and advantages will be apparent from the description, drawings, and the claims.

BRIEF DESCRIPTION OF THE DRAWINGS

The accompanying drawings, which are incorporated in and constitute a part of this specification, and in which corresponding reference characters indicate corresponding parts in each of the several views, illustrate embodiments of the disclosure and, together with a general description of the disclosure given above, and the detailed description of the embodiment(s) given below, serve to explain the principles of the disclosure, wherein.

DETAILED DESCRIPTION

In this disclosure, the term "distal" refers to a portion of a structure that is farther from a clinician, while the term "proximal" refers to a portion of the same structure that is closer to the clinician. As used herein, the term "subject" refers to a human patient or other animal. The term "clinician" refers to a doctor (e.g., a surgeon), nurse, or other care provider, and may include support personnel.

Figure 1:
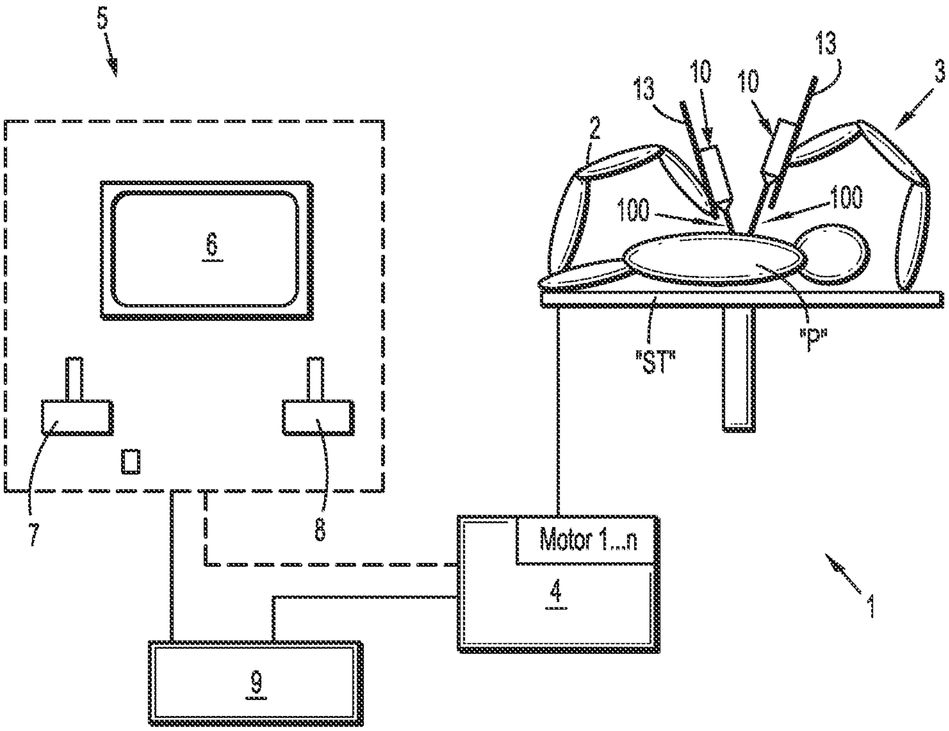
FIG. 1 is a schematic illustration of a robotic surgical system including a surgical assembly in accordance with the present disclosure.

Referring initially to FIG. 1, a robotic surgical system, such as, for example, medical work station 1, generally includes a plurality of robot arms 2 and 3, a control device 4, and an operating console 5 coupled with control device 4. Operating console 5 includes a display device 6, which is set up in particular to display three-dimensional images, and manual input devices 7 and 8, by means of which a clinician (not shown), for example a surgeon, is able to telemanipulate robot arms 2 and 3 in a first operating mode, as known in principle to a person skilled in the art.

Each of the robot arms 2 and 3 includes a plurality of members, which are connected through joints, to which may be attached, for example, a surgical assembly 10. Robot arms 2 and 3 may be driven by electric drives (not shown) that are connected to control device 4. Control device 4 (e.g., a computer) is set up to activate the drives, in particular by means of a computer program, in such a way that robot arms 2 and 3, the attached surgical assembly 10, and thus the surgical instrument 100 (including the end effector, not shown) execute a desired movement according to a movement defined by means of manual input devices 7 and 8.

Control device 4 may also be set up in such a way that it regulates the movement of robot arms 2 and 3 and/or of the drives (not shown). Control device 4 may control a plurality of motors, e.g., "Motor 1 . . . n," with each motor configured to drive movement of robotic arms 2 and 3 in a plurality of directions.

Medical work station 1 is configured for use on a patient "P" lying on a surgical table "ST" to be treated in a minimally invasive manner by means of a surgical instrument 100 of surgical assembly 10. Medical work station 1 may also include more than two robot arms 2 and 3, the additional robot arms likewise being connected to control device 4 and being telemanipulatable by means of operating console 5. A surgical assembly 10 may also be attached to the additional robot arm. Medical work station 1 may include a database 9, in particular coupled to with control device 4, in which are stored for example pre-operative data from patient "P" and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Figure 2:
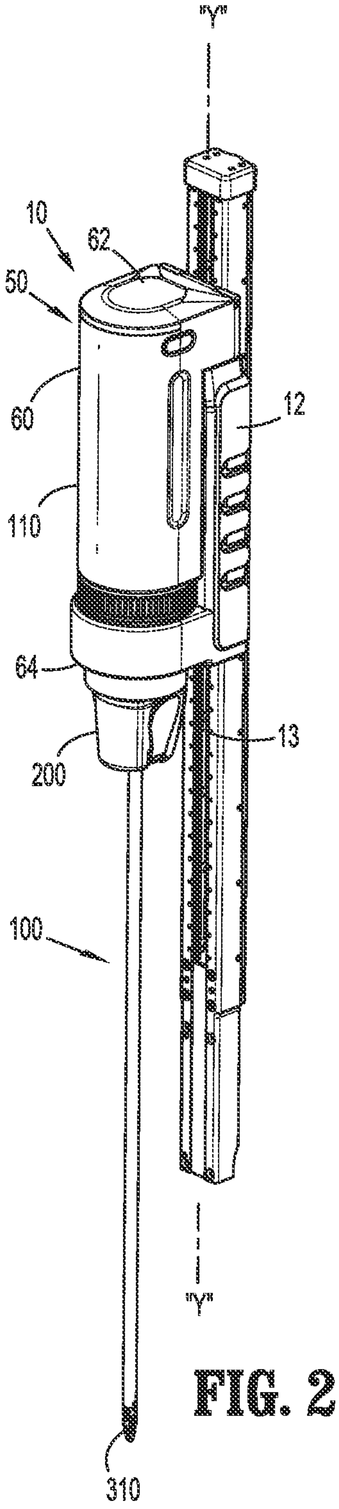
FIG. 2 is a perspective view of a surgical assembly of the robotic surgical system of FIG. 1.

Turning now to FIG. 2, in conjunction with FIG. 1, surgical assembly 10 is shown coupled with or to robotic arm 2. While surgical assembly 10 is discussed singularly, a person of ordinary skill in the art can readily appreciate that the medical work station 1 may also include a plurality of substantially identical surgical assemblies 10 coupled with or to each of the robotic arms 2 and 3. Surgical assembly 10 includes an instrument drive unit 50 coupled to an instrument drive connector 200 of a surgical instrument 100 having an end effector 310 disposed at a distal end thereof.

Instrument drive unit 50 of surgical assembly 10 may be supported on or connected to a slider 12 that is movably connected to a track or slide 13 of robotic arm 2. Slider 12 moves, slides, or translates along a longitudinal axis "Y" defined by track 13 of surgical robotic arm 2 upon a selective actuation by motors (not shown) disposed in track 13 of robotic arm 2 or motors (e.g., one or more of "Motor 1 . . . n") of control device 4. As such, slider 12, with instrument drive unit 50 connected thereto, can be moved to a selected position along track 13 of robotic arm 2.

Figure 3:
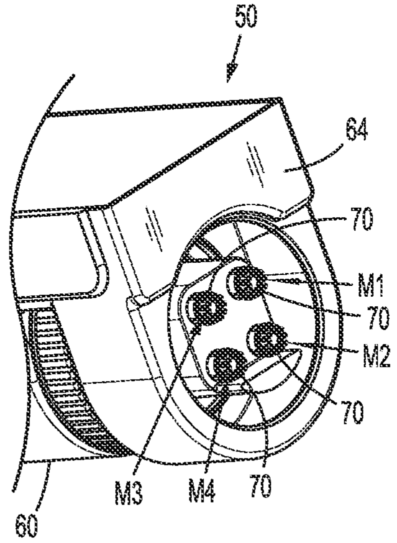
FIG. 3 is a perspective, end view of an instrument drive unit of the surgical assembly of FIG. 2.
Figure 4:
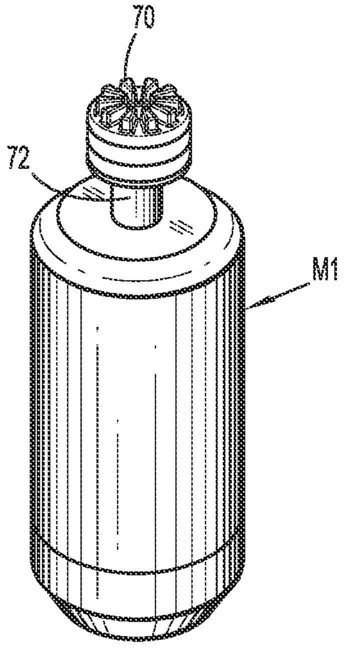
FIG. 4 is a schematic, perspective view of a motor of the instrument drive unit of FIG. 3.

With reference now to FIGS. 2 and 3, instrument drive unit 50 of surgical assembly 10 includes a housing 60 having a proximal end 62 and a distal end 64 configured to be operably coupled to instrument drive connector 200 of surgical instrument 100. Housing 60 of instrument drive unit 50 houses a plurality of motors "M1-M4" that are configured to drive various operations of end effector 310 of surgical instrument 100. Each motor "M1-M4" of instrument drive unit 50, as shown in an exemplary illustration of motor "M1" in FIG. 4, includes an output drive coupler 70 supported on a rotatable shaft 72 extending distally from the motor. In some embodiments, output drive couplers 70 are crown gears or the like, that are keyed to or non-rotatably supported on rotatable shafts 72 of at least one of motors "M1-M4." In use, instrument drive unit 50 transfers power and actuation forces from its motors (e.g., "M1-M4") to instrument drive connector 200 of surgical instrument 100 via rotation of output drive coupler(s) 70 to ultimately drive movement of components of end effector 310 of surgical instrument 100, as described in further detail below.

Control device 4 (FIG. 1) may control motors "M1-M4" of instrument drive unit 50. In some embodiments, at least one motor "M1-M4" receives signals wirelessly (e.g., from control device 4). It is contemplated that control device 4 coordinates the activation of the various motors ("Motor 1 . . . n") to coordinate an operation and/or movement of surgical instrument 100. It is envisioned that one or more motors correspond to a separate degree of freedom of surgical instrument 100 engaged with instrument drive unit 50.

Figure 5:
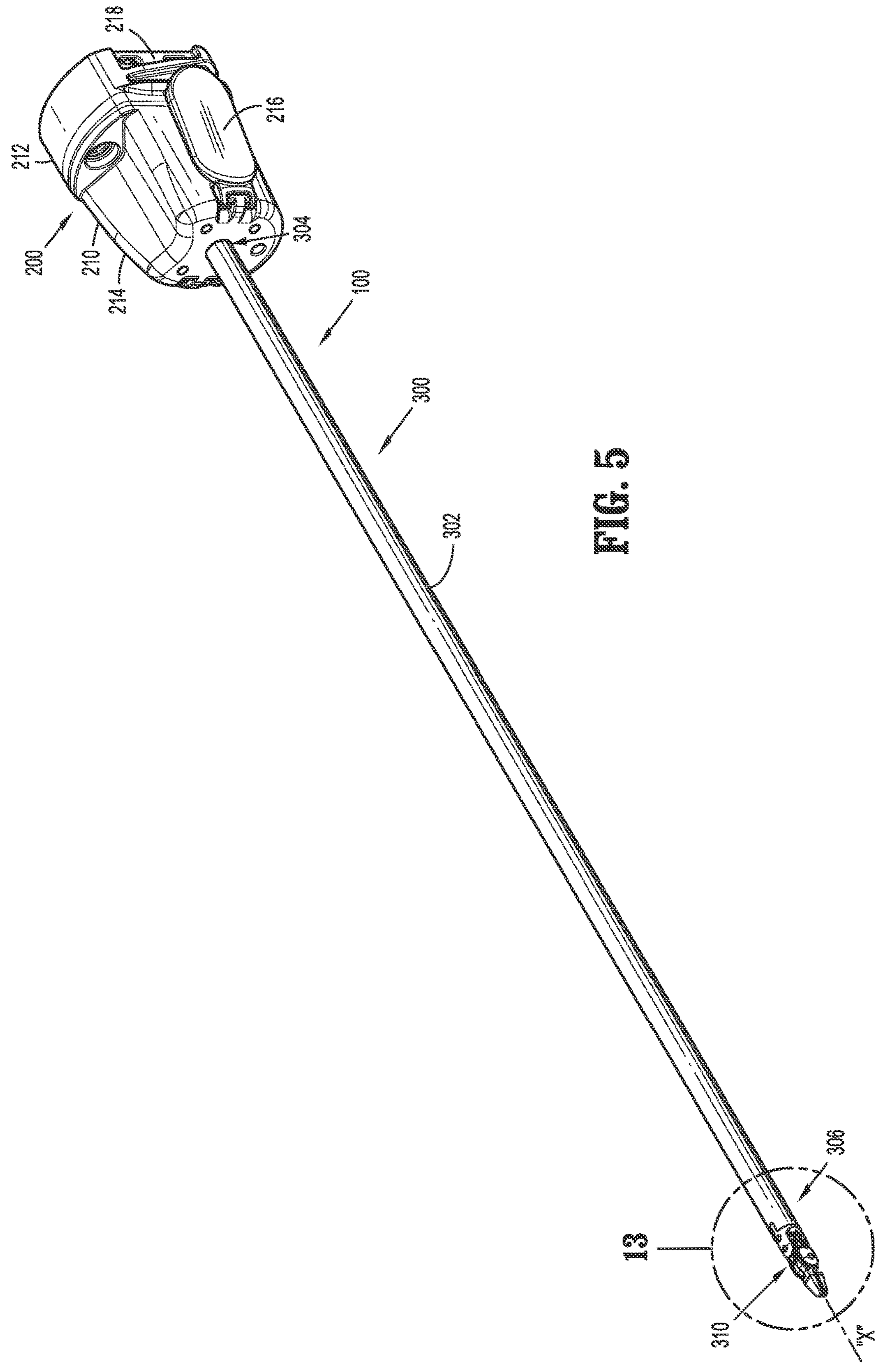
FIG. 5 is a perspective view of a surgical instrument of the surgical assembly of FIG. 2 including an instrument drive connector.
Figure 6:
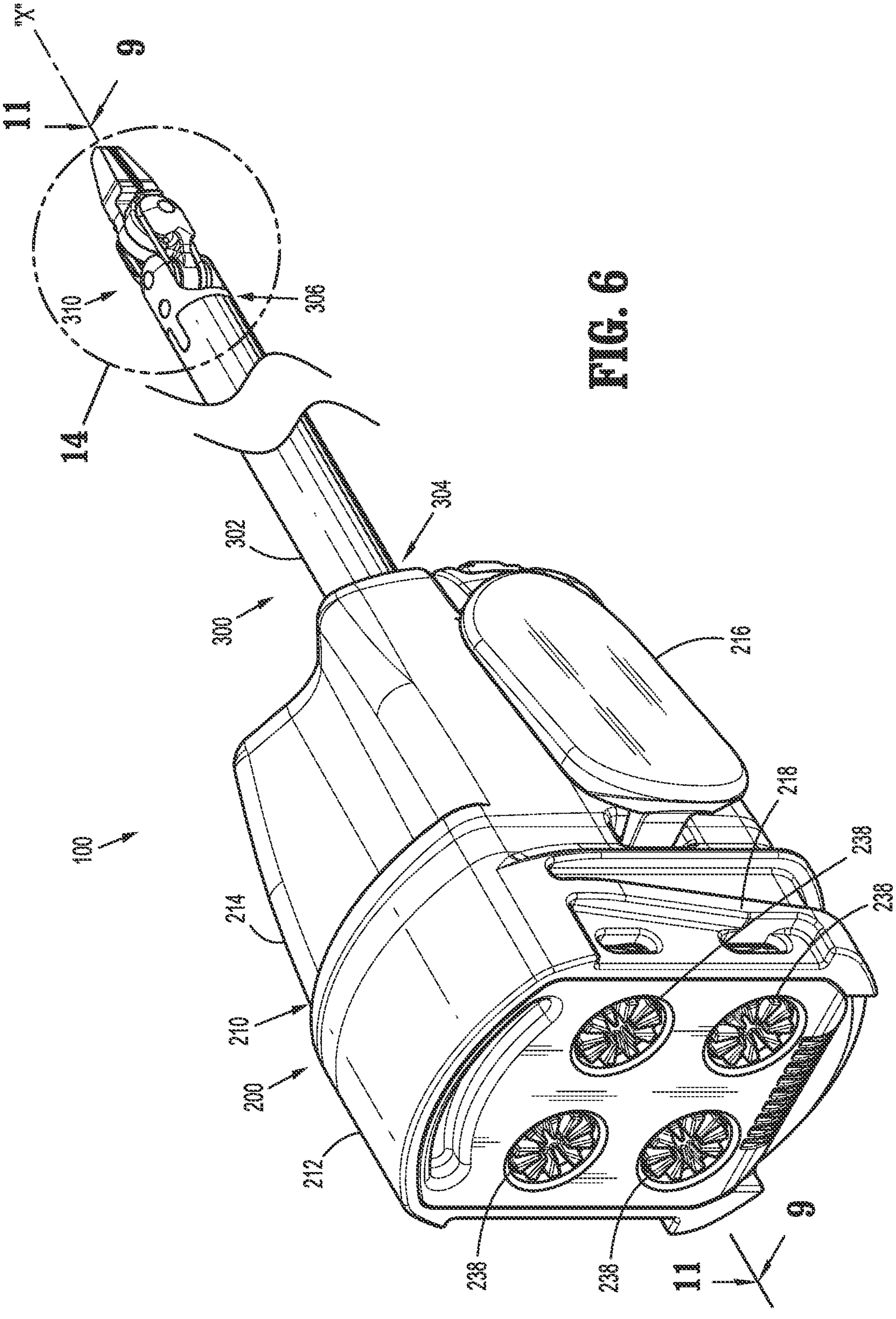
FIG. 6 is an enlarged perspective view of the surgical instrument of FIG. 5.
Figure 7:
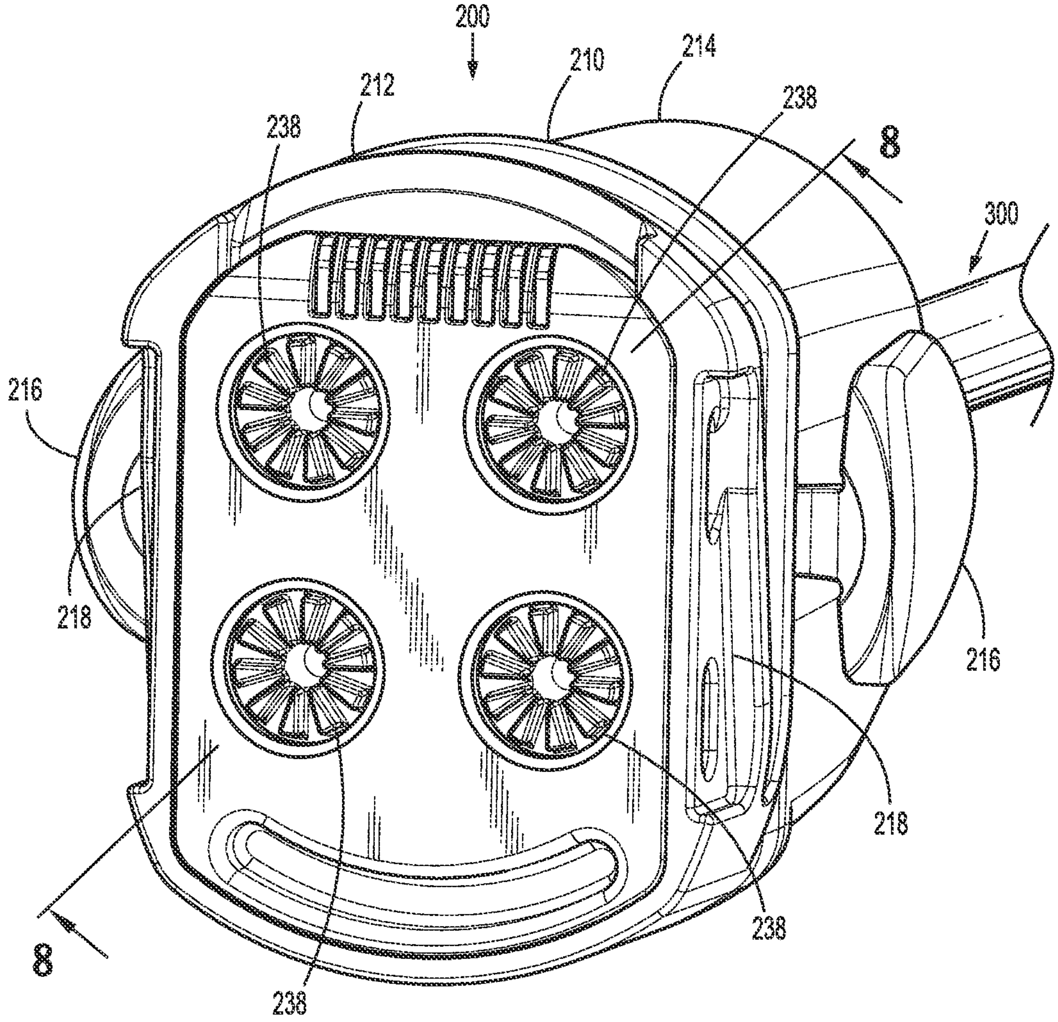
FIG. 7 is a perspective, end view of an instrument drive connector of the surgical instrument of FIGS. 5 and 6.

Referring now to FIGS. 5-7, instrument drive connector 200 of surgical assembly 10 includes a housing assembly 210 which includes a proximal housing 212 and a distal housing 214. Proximal housing 212 and distal housing 214 are releasably coupled to each other, which may facilitate assembly of instrument drive connector 200, and which may facilitate access, repair, and/or replacement of parts housed at least partially therein. Housing assembly 210 may include cantilevered arms 216 configured for use in disconnecting instrument drive connector 200 from distal end 64 of housing 60 of instrument drive unit 50. Proximal housing 212 of housing assembly 210 includes ramped camming surfaces 218 disposed on opposed side surfaces thereof for transverse connection/disconnection with complementary mating surfaces (not shown) of instrument drive unit 50 (FIG. 2).

With reference now to FIGS. 8-12, housing assembly 210 defines a bore 211 which houses a plurality of drive assemblies 220 supported by a drive assembly frame 270. Each drive assembly 220 includes a drive screw 230, a drive nut 240, and a biasing element 250, and is operatively connected to a drive member or rod 260. Drive assembly frame 270 includes a proximal end 272 having a plurality of proximal bearings 274 in which proximal ends 232 of drive screws 230 are retained. Each proximal bearing 274 permits or facilitates rotation of drive screw 230 with respect to housing assembly 210. Additionally, proximal bearings 274 may be configured to function as a proximal stop for drive nut 240. Proximal bearings 274 are disposed radially around a proximal end of an elongated central shaft 276. A plurality of longitudinally extending grooves 278 (FIG. 10) are defined in an outer surface **276*a* of central shaft 276. Each groove 278 is configured to slidingly engage a proximal end portion 262 of drive members 260 and second rail 248 of drive nut 240**.

Figure 12:
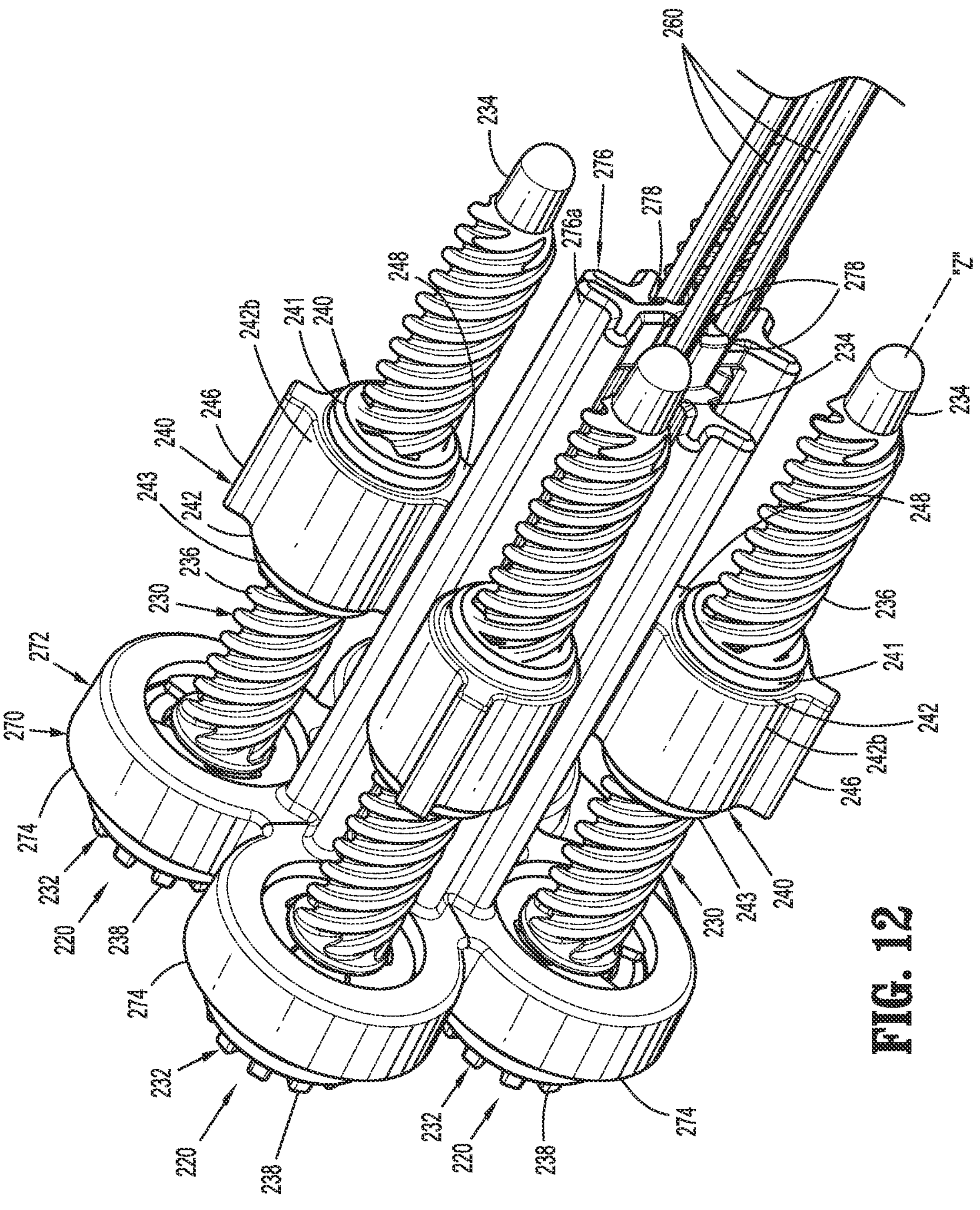
FIG. 12 is a perspective view of a drive assembly disposed within the instrument drive connector of FIGS. 5-11.

As shown in FIG. 12, drive screw 230 includes a proximal end 232, a distal end or tip 234 that is non-threaded, and an elongated threaded body 236 extending between proximal and distal ends 232 and 234, and defines a longitudinal axis "Z" through a radial center thereof. Proximal end 232 of drive screw 230 includes an input drive coupler 238 that is configured to engage with respective output drive couplers 70 of instrument drive unit 50 (FIG. 3) such that movement of output drive couplers 70 cause a corresponding movement of input drive coupler 238. As input drive coupler 238 is monolithically formed with elongated threaded body 236, rotation of input drive coupler 238 results in a corresponding rotation of elongated threaded body 236. It should be understood that input drive coupler 238 and elongated threaded body 236 may be separate components that are keyed to one another. In some embodiments, input drive coupler 238 may be a gear, such as a crown gear, that is configured to mate and/or mesh with a respective crown gear 70 of motor "M1-M4" (FIG. 3), such that rotation of crown gear 70 causes a corresponding rotation of crown gear 238.

Figure 8:
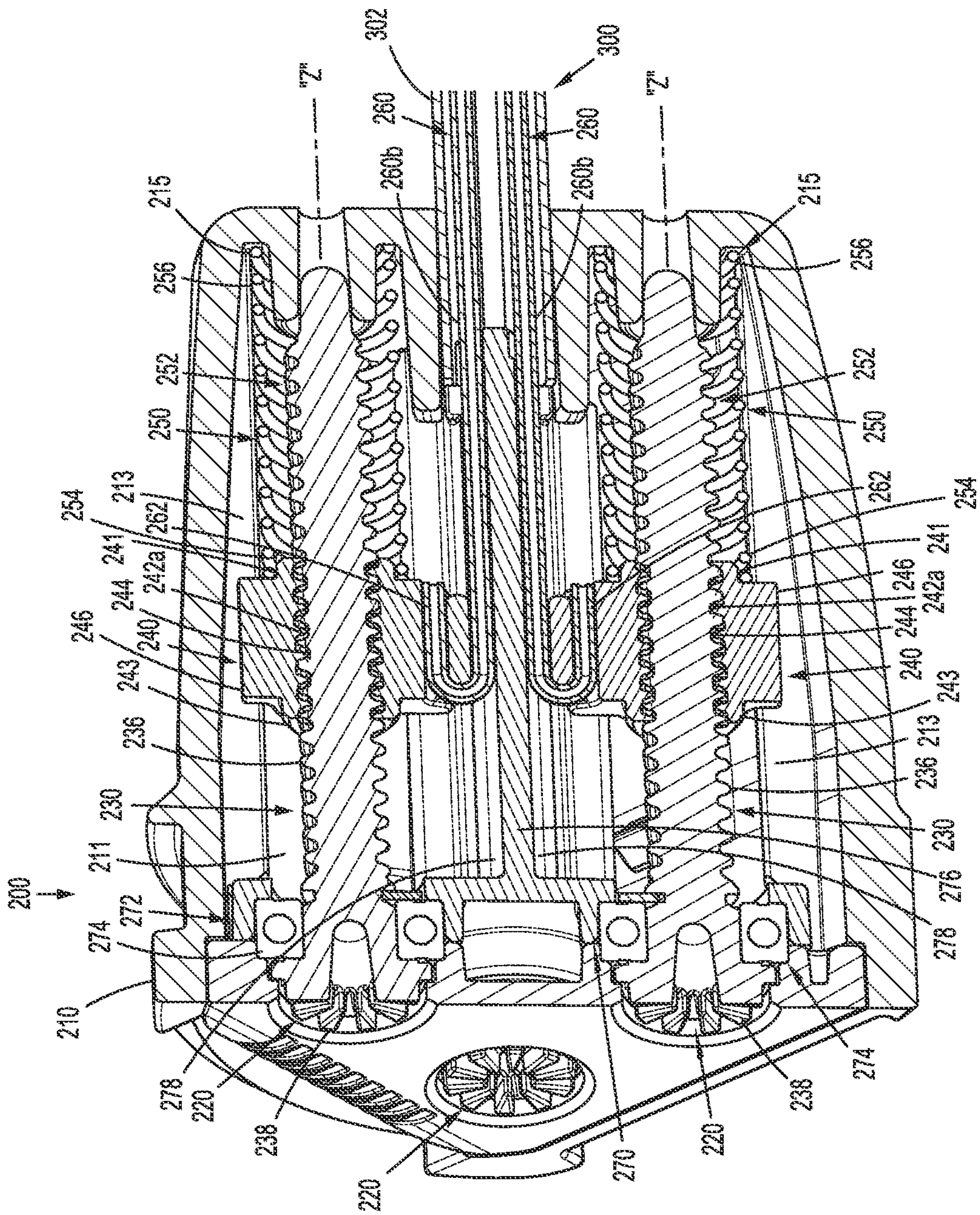
FIG. 8 is a cross-sectional view of the instrument drive connector of the surgical instrument of FIGS. 5-7, taken along line 8-8 of FIG. 7.

As shown in FIGS. 8 and 12, drive nut 240 includes a body 242 having a threaded aperture 244 extending longitudinally through an inner surface **242*a* thereof which is configured to mechanically engage the elongated threaded body 236 of drive screw 230. Drive nut 240 is configured to be positioned on drive screw 230 in a manner such that rotation of drive screw 230 causes longitudinal movement of drive nut 240. In embodiments, drive nut 240 and drive screw 230 are threadedly engaged with each other. Moreover, rotation of input drive coupler 238 in a first direction (e.g., clockwise) causes drive nut 240 to move in a first longitudinal direction (e.g., proximally) with respect to drive screw 230, and rotation of input drive coupler 238 in a second direction (e.g., counter-clockwise) causes drive nut 230 to move in a second longitudinal direction (e.g., distally) with respect to drive screw 230**.

Drive nut 240 includes a first rail 246 extending longitudinally along an outer surface 242*b* of body 242, and which is configured to be slidably disposed in a longitudinally extending channel 213 formed in bore 211 of housing assembly 210. First rail 246 of drive nut 240 cooperates with channel 213 of bore 211 of housing assembly 210 to inhibit or prevent drive nut 240 from rotating about longitudinal axis "Z" as drive screw 230 is rotated. Drive nut 240 also includes a second rail 248 extending longitudinally along an outer surface 242*b* of body 242 which is configured to be slidably disposed in longitudinally extending groove 278 formed in drive assembly frame 270. Second rail 248 is configured to mechanically engage a proximal end portion 262 of drive member 260.

Drive nut 240 also includes a retention flange 241 disposed at a distal end of body 242. Retention flange 241 has a smaller outer diameter than body 242 of drive nut 240 and is configured to engage a portion of biasing element 250. Additionally or alternatively, a retention flange 243 may be disposed at a proximal end of body 242 of drive nut 240.

A biasing element 250, e.g., a compression spring, is configured to radially surround a portion of elongated threaded body 236 of drive screw 230. In embodiments, drive screw 230 extends through an aperture 252 defined by and extending longitudinally through biasing element 250. Additionally, as seen in FIG. 8, a proximal portion 254 of biasing element 250 is configured and dimensioned to engage retention flange 241 of drive nut 230 and a distal portion 256 of biasing element 250 is configured and dimensioned for reception at least partially within a retention pocket 215 formed in bore 211 of housing assembly 210. While the illustrated embodiment shows a particular type of biasing element (i.e., a compression spring), other types of biasing elements are contemplated by the present disclosure. Further still, it is contemplated that other retaining structures may be utilized for engagement with a biasing element.

Figure 9:
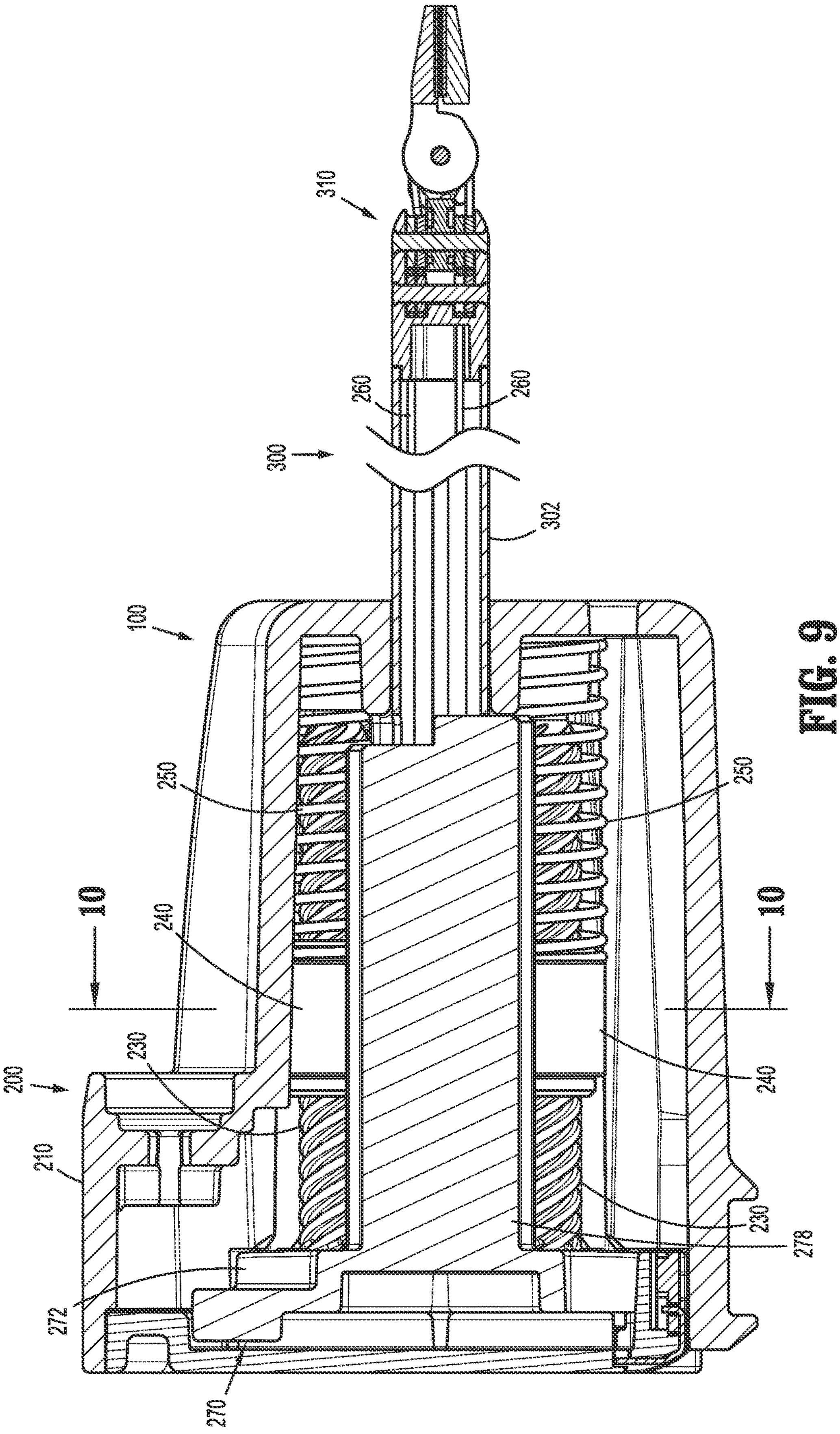
FIG. 9 is a cross-sectional view of the instrument drive connector of the surgical instrument of FIGS. 5-8, taken along line 9-9 of FIG. 6.
Figure 10:
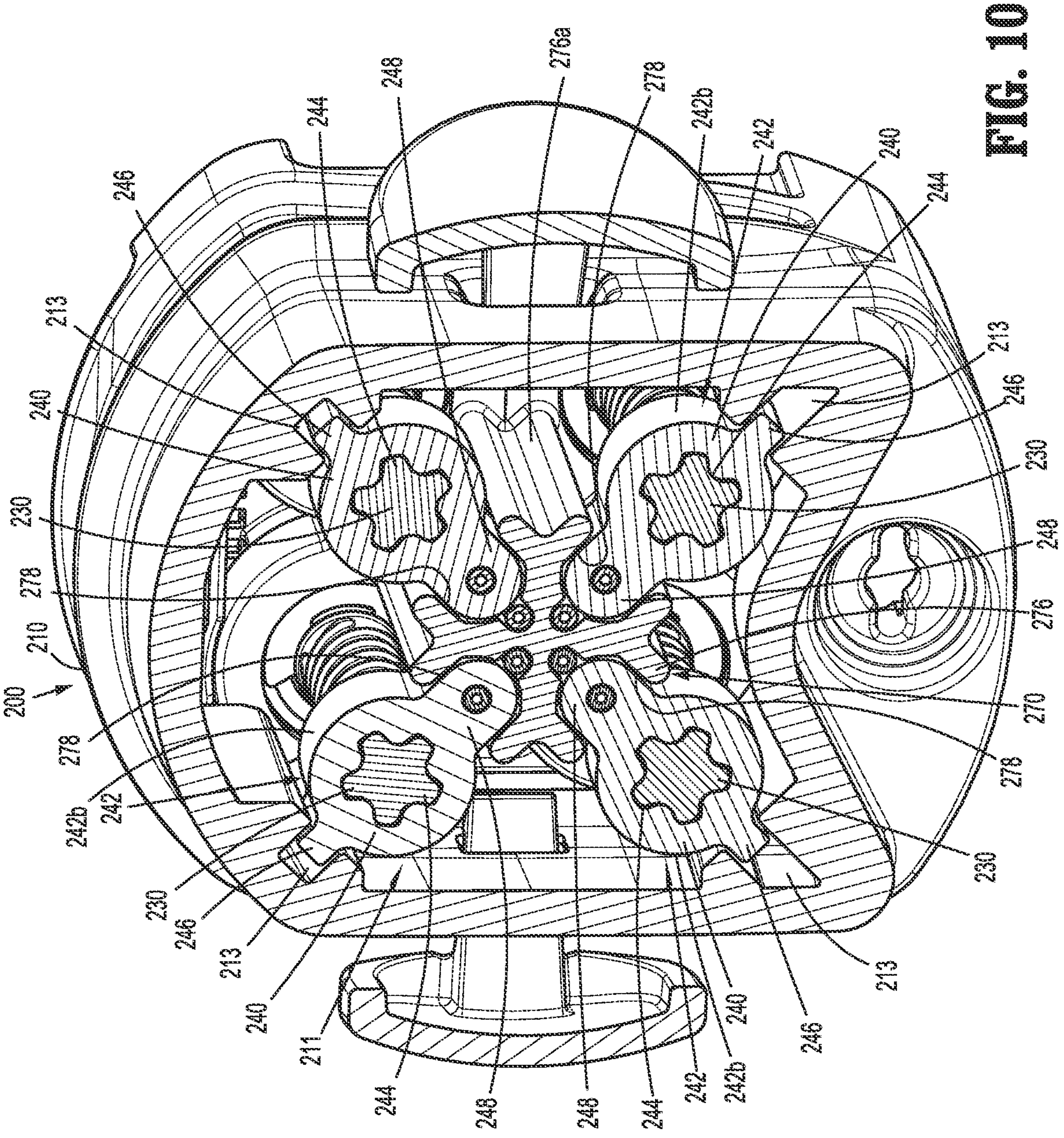
FIG. 10 is a perspective, cross-sectional view of the instrument drive connector of the surgical instrument of FIGS. 5-9, taken along line 10-10 of FIG. 9.
Figure 11:
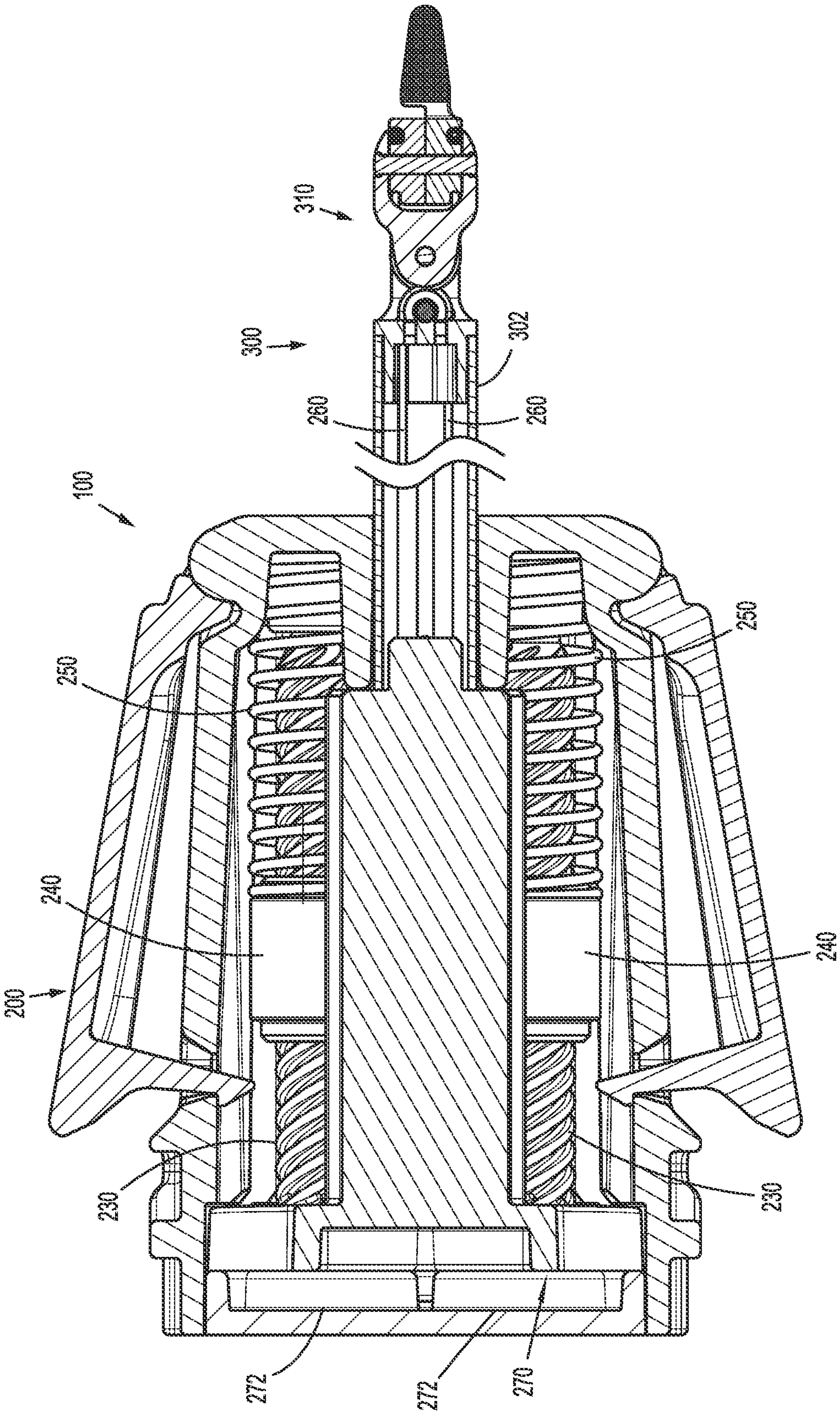
FIG. 11 is a cross-sectional view of the instrument drive connector of the surgical instrument of FIGS. 5-10, taken along line 11-11 of FIG. 6.

Each drive member 260 (e.g., cables, chains, belts, rods, etc. and/or combinations thereof) includes a proximal end portion 262 secured to a respective drive nut 240. Each drive member 260 extends from a respective drive nut 240, through a respective groove 278 of drive assembly frame 270, and out bore 211 of housing assembly 210, and is configured to mechanically engage a portion of end effector 310 (FIG. 9).

Biasing element 250 is pre-tensioned to push a respective drive nut 240 in a proximal direction, thereby applying tension to the respective drive member 260 and preventing drive member 260 from going slack. Drive screw 230, around which biasing element 250 is disposed, is thus back-drivable allowing for manual operation when instrument drive unit 50 is not connected to instrument drive connector 200. Accordingly, when the instrument drive unit 50 is not connected the instrument drive connector 200, a clinician may manually rotate input drive coupler(s) 238 of instrument drive connector 200 to control the surgical instrument 100. For example, when surgical instrument 100 is being retracted from, for example, an access port, and if wrist assembly 320 and/or jaw assembly 330 are in a configuration that would not pass through the orifice formed by the access port, the back-drivability of the drive screws 230 allows wrist assembly 320 and/or jaw assembly 330 to be moved and/or straighten for easy removal of surgical instrument 100 from a patient. As another example, the back-drivability allows for easy manipulation during cleaning of surgical instrument 100 between uses.

Each drive assembly 220 is oriented within housing assembly 210 such that the drive members 260 are centrally located within housing assembly 210, and extends through an elongated shaft 302 of surgical instrument 100 and into engagement with end effector 310, for example. It is envisioned that surgical instrument 100 may include projections or the like to help guide or route drive members 260 between drive assembly 220 and end effector 310.

With reference again to FIGS. 5 and 6, instrument drive connector 200 is configured to transfer rotational movement supplied by instrument control unit 50 (see e.g., FIG. 2) into longitudinal movement of drive members 260 (see e.g., FIG. 8) to effect various functions of end effector 310.

Figure 13:
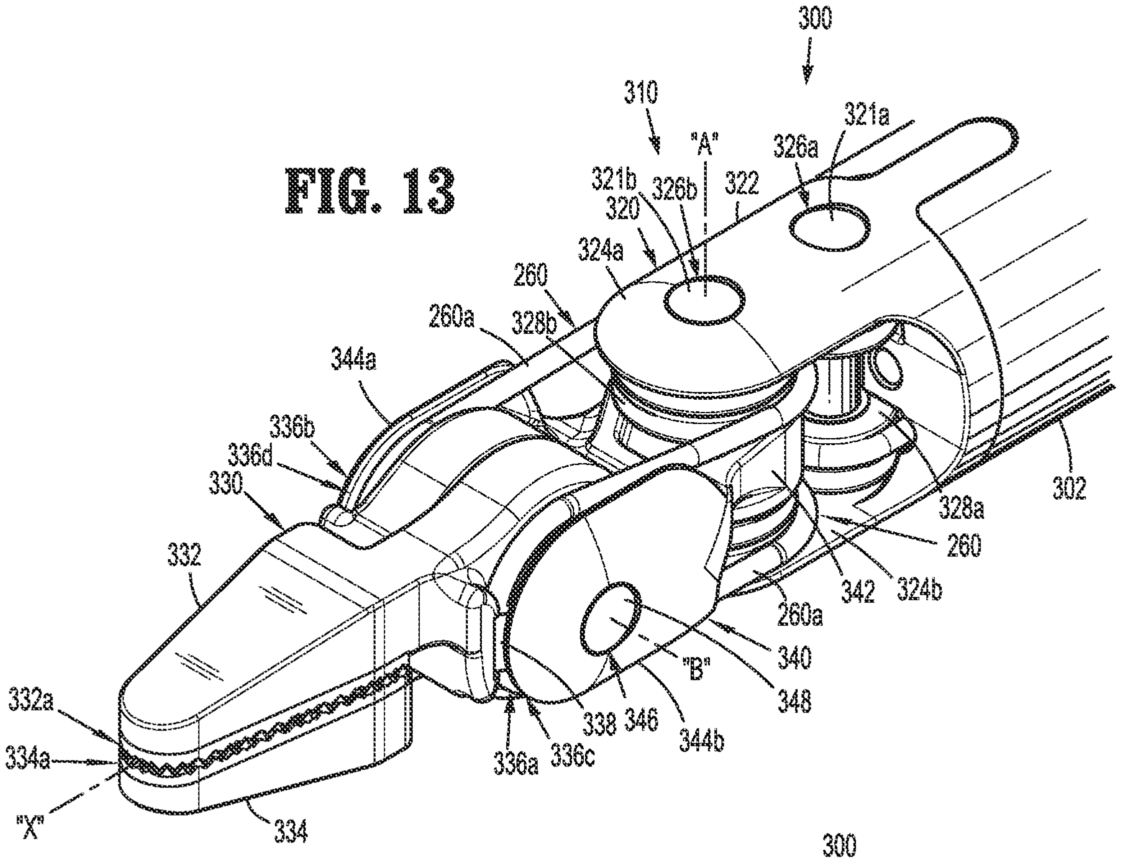
FIG. 13 is enlarged view of the area of detail indicated in FIG. 5.
Figure 14:
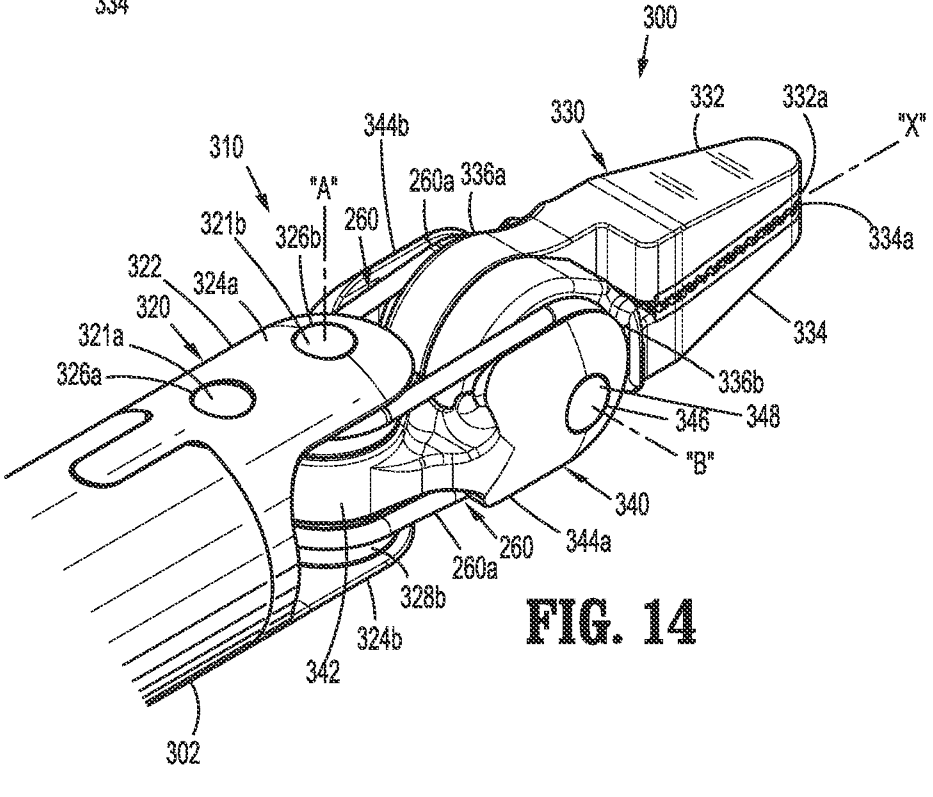
FIG. 14 is enlarged view of the area of detail indicated in FIG. 6.
Figure 15:
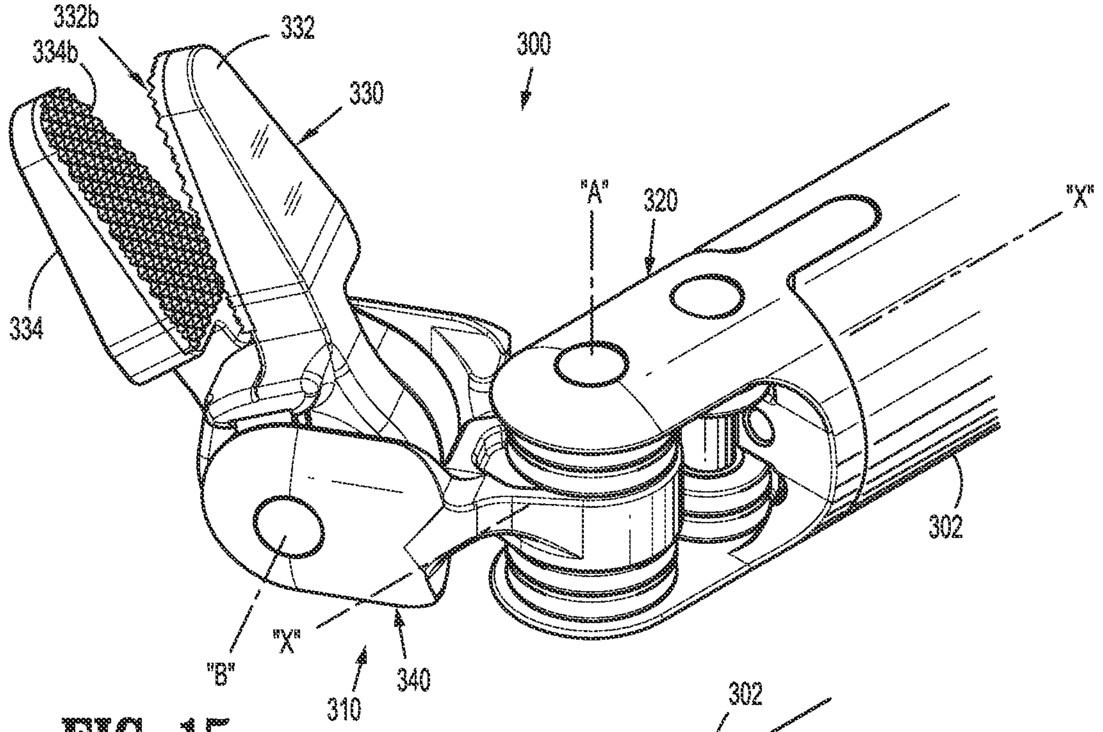
FIG. 15 is a perspective view of an end effector of the surgical instrument of FIGS. 5, 6, 13, and 14 with drive members removed therefrom.

Referring now to FIGS. 13-15, in conjunction with FIGS. 5 and 6, surgical instrument 100 includes an endoscopic portion 300 including an elongated shaft 302 extending along longitudinal axis "X." Elongated shaft 302 includes a proximal portion 304 operably connected to or integrally formed with instrument drive connector 200 and a distal portion 306 having an end effector 310. End effector 310 is a wristed surgical device including a mounting member or wrist assembly 320, a jaw assembly 330, and a clevis 340 connecting the wrist assembly 320 with the jaw assembly 330. Wrist assembly 320 and clevis 340 are connected to jaw assembly 330 which moves (e.g., pivots, articulates, rotates, opens, and/or closes) about/relative to longitudinal axis "X" and/or about/relative to pivot axes, such as axis "A" and "B," upon movement of drive member(s) 260.

Wrist assembly 320 has a mount body 322 that extends distally to a pair of spaced-apart arms including a first arm 324*a* and a second arm 324*b*. The pair of spaced-apart arms 324*a* and 324*b* defines a first pin channel 326*a* and a second pin channel 326*b* that extend transversely through each of first and second arms 324*a* and 324*b*. Wrist assembly 320 supports a first set of idler pulleys 328*a* and a second set of idler pulleys 328*b* that are aligned with first and second pin channels 326*a* and 326*b*, respectively, such that the first set of idler pulleys 328*a* is located proximal of second set of idler pulleys 328*b*. First and second sets of idler pulleys 328*a* and 328*b* are secured to wrist assembly 320 via first and second pulley pins 321*a* and 321*b*, respectively. Second pulley pin 328*b* and second set of idler pulleys 326*b* define a pivot axis "A" about which first and second jaw members 332 and 334 pitch relative to longitudinal axis "X."

Jaw assembly 330 includes a first jaw member 332 and a second jaw member 334 that are pivotably coupled together. First jaw member 332 includes a grasping portion 332*a* that extends distally from a first jaw pulley 336*a*. Second jaw member 334 includes a grasping portion 334*a* that extends distally from as second jaw pulley 336*b*. First and second jaw pulleys 336*a* and 336*b* may be integrally formed with grasping portions 332*a*, 334*a*, respectively, of first and second jaw members 332 and 334. Grasping portions 332*a* and 334*a* include respective tissue-engaging surfaces 332*b*, 334*b* configured to engage tissue. First and second jaw pulleys 336*a* and 336*b* define respective first and second drive member channels 336*c* and 336*d* configured to receive drive members 260.

Clevis 340 includes a base portion 342 having a pair of spaced-apart fingers 344*a* and 344*b* that extend distally from base portion 342. The pair of spaced-apart fingers 344*a* and 344*b* define a pin passage 346 that extends transversely therethrough. Base portion 342 is pivotally mounted to second set of idler pulleys 326*b* by pivot pin 321*b* to enable jaw assembly 330 to pitch/articulate relative to a longitudinal axis “X” of end effector 310. Jaw pulleys 336*a* and 336*b* of jaw assembly 300 are coupled together and mounted between the pair of fingers 344*a* and 344*b* of clevis 340 by pivot pin 348 to enable jaw assembly 330 to yaw about pivot axis “B” and/or to open/close jaw assembly 330 about pivot axis “B.”

As shown in FIGS. 13 and 14, each drive member 260 includes a distal drive member portion 260*a* (in the form of a cable or the like) that is routed/wrapped around the set of idler pulleys 328*a* and 238*b* and jaw pulleys 336*a* and 336*b*. Each drive member 260 further includes a proximal drive member portion 260*b* (in the form of a rod) that is individually secured to a respective drive nut 240 (see e.g., FIG. 8) of drive assembly 220 so that proximal drive member portion 260*b* moves in response to movement of respective drive nut 240, as described above. A plurality of ferrules 338 (only one being shown) are coupled to the distal drive member portion 260*a* of drive member 260 to secure distal drive member portion 260*a* to first jaw member 332 or second jaw member 334 of jaw assembly 330.

In an exemplary method of use, when motor(s) “M1-M4” of instrument drive unit 50 are activated in coordination with one another to rotate (clockwise or counterclockwise) input drive coupler(s) 238 of instrument drive connector 200, rotation of input drive coupler(s) 238 results in a corresponding rotation of respective drive screw(s) 230. Rotation of drive screw(s) 230 causes longitudinal translation (distal or proximal) of respective drive nut(s) 240, with the direction of longitudinal translation of each drive nut 240 being determined by the direction of rotation of its respective output drive coupler 238, and thus drive screw 230. Translation of drive nut(s) 240 results in a corresponding translation of respective drive member(s) 260 which are engaged with drive nut(s) 240.

Figure 16:
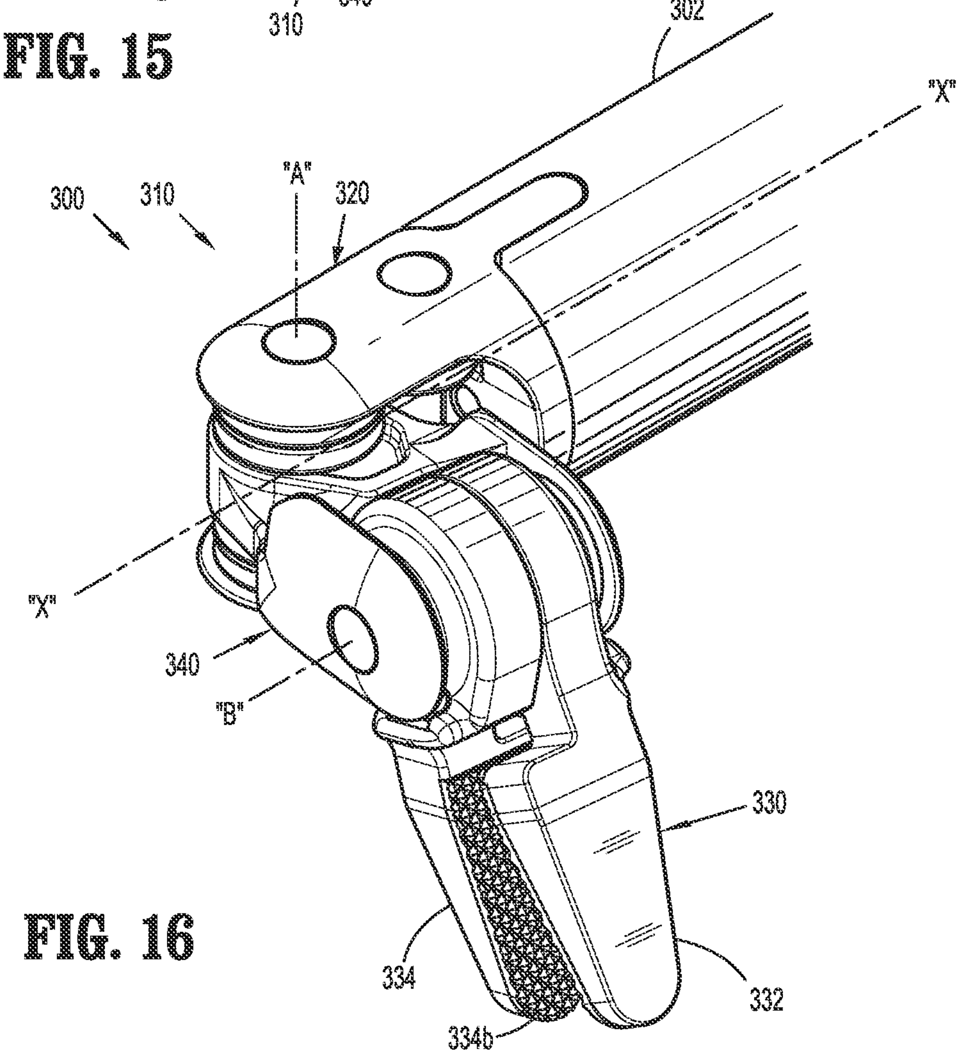
FIG. 16 is a perspective view of the end effector of the surgical instrument of FIGS. 5, 6, and 13-15 with drive members removed therefrom.

Accordingly, one or more of proximal drive member portions 260*b* of drive members 260 can be moved independently of and/or simultaneously with one or more of the other proximal drive member portions 260*b* of drive member 260 in the same and/or in opposite directions to effectuate pitching, yawing, grasping/dissecting, opening/closing, and/or any combination of these motions of end effector 310, as shown for example in FIGS. 15 and 16. In some embodiments, drive assemblies 220 utilize differential tension of drive members 260 to effect operation and/or movement of end effector 310 of surgical instrument 100.

While certain embodiments have been described, other embodiments are possible.

Figure 17:
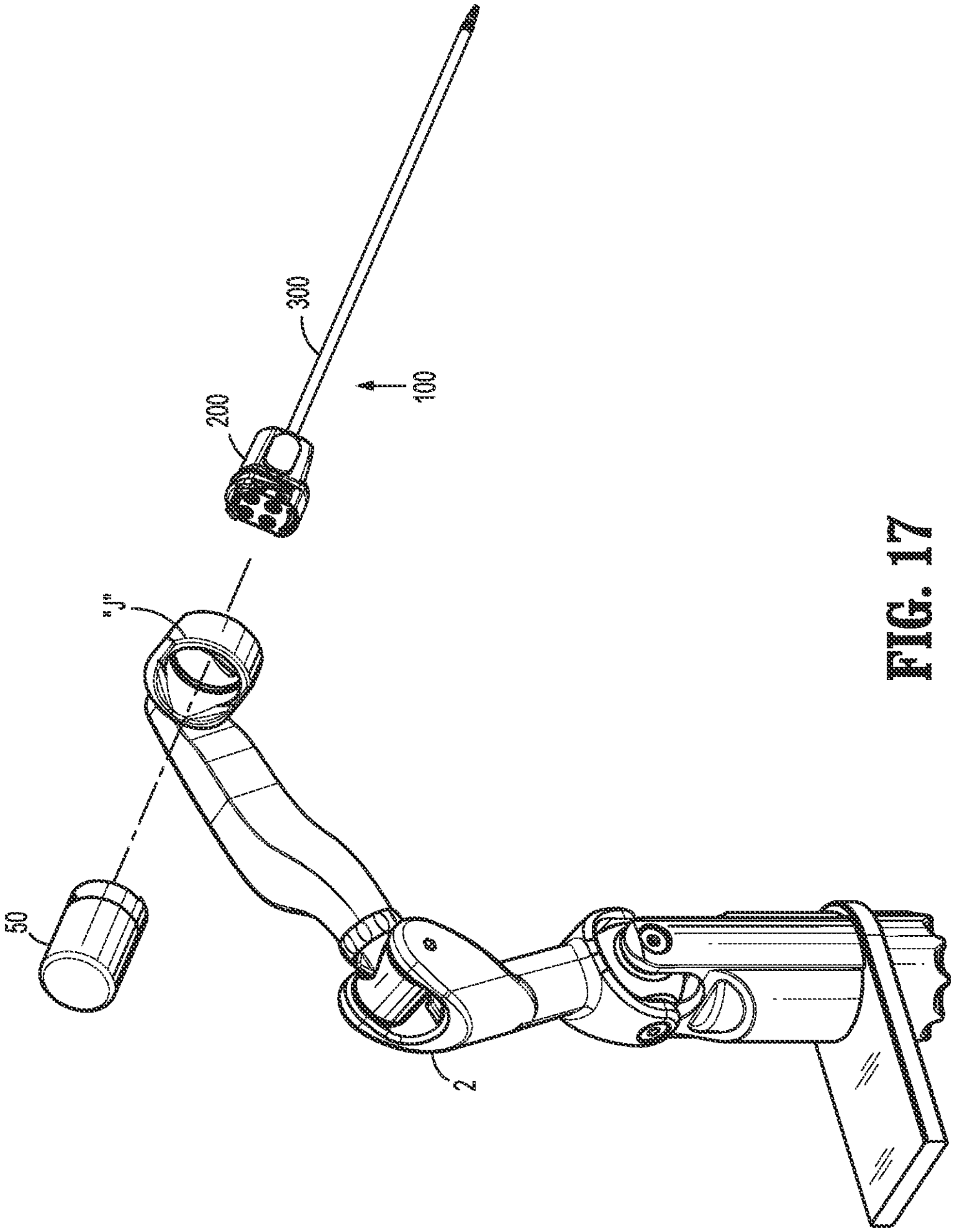
FIG. 17 is a perspective view of a robotic arm of a robotic surgical system including a surgical assembly with parts separated in accordance with the present disclosure.

For example, while instrument drive units have been described as being movably connected to a track of a robotic arm, other configurations are additionally or alternatively possible. For example, as shown in FIG. 17, instrument drive unit 50 may be directly coupled to a joint “J” disposed at a distal end of robotic arm 2. Instrument drive connector 200 of surgical instrument 100 may be connected/disconnected to instrument drive unit 50, as described above.

As another example, while instrument drive connectors have been described as including four drive assemblies, instrument drive connectors may include more (e.g., five or six) or fewer (e.g., two or three) drive assemblies without departing from the scope of the present disclosure.

Additionally, while drive assembly frames have been described as being a component of a drive assembly, the entire structure of a drive assembly frame, or portions thereof, may be integrally formed within the housing assembly of an instrument drive connector.

As still another example, while end effectors have been described as including a jaw assembly, the use of other end effectors are additionally or alternatively possible. Reference may be made to commonly owned International Patent Application No. PCT/US14/61329, filed on Oct. 20, 2014 entitled “Wrist and Jaw Assemblies for Robotic Surgical Systems,” the entire content of which is incorporated herein by reference, for a detailed discussion of illustrative examples of the construction and operation of end effectors for use with an instrument drive unit.

As yet another example, while two proximal end portions of a single drive member are shown coupled to separate drive nuts, it is contemplated that two or more proximal end portions of two or more drive members or two proximal end portions of a single drive member may be coupled to a single drive nut. For example, two proximal end portions of a drive member may be coupled in opposite directions to a single drive nut so that as the drive nut is translated in a first direction, one of the proximal end portions winds up while the other proximal end portion lets out.

As another example, each drive assembly may include a drive member in mechanical cooperation with a drive nut and the end effector, such that each drive member includes a single proximal end portion connected to a drive nut and a distal end portion coupled to an end effector to effect a function of the end effector. For example, distal translation of a particular drive member may be configured to approximate jaw members with respect to each other and proximal translation may be configured to move at least one jaw member away from the other jaw member. Further, distal translation of a drive member of a different drive assembly may be configured to articulate jaw members in a first direction, and proximal translation of the same drive member may be configured to articulate jaw members in a second direction.

A number of embodiments have been described. Nevertheless, it will be understood that various modifications may be made to the embodiments disclosed herein. Therefore, the above description should not be construed as limiting, but merely as exemplifications of various embodiments. Those skilled in the art will envision other modifications within the scope and spirit of the disclosure. Accordingly, other embodiments are within the scope of the following claims.

What is claimed is:

1. A surgical instrument for use with a robotic surgical system, the surgical instrument comprising:

- an instrument drive connector including a housing assembly defining a bore therein;
- an elongated shaft having a proximal portion operably coupled to the instrument drive connector and a distal portion having an end effector; and
- a drive assembly housed within the bore of the housing assembly, the drive assembly including:
  - a drive screw rotatable relative to the housing assembly;
  - a drive nut mechanically engaged with the drive screw such that rotation of the drive screw causes longitudinal movement of the drive nut;
  - a biasing element surrounding a portion of the drive screw; and
  - a drive member in mechanical cooperation with the drive nut and the end effector.

2. The surgical instrument according to claim 1, wherein the drive screw includes a proximal end having an input drive coupler configured to receive rotational forces.

3. The surgical instrument according to claim 1, wherein the drive nut includes a first rail extending longitudinally along an outer surface thereof, the first rail slidingly disposed within a longitudinally extending channel formed within the housing assembly.

4. The surgical instrument according to claim 1, wherein the instrument drive connector includes a drive connector frame disposed within the housing assembly and in mechanical cooperation with the drive assembly.

5. The surgical instrument according to claim 4, wherein the drive connector frame includes a proximal end including a proximal bearing dimensioned to retain a proximal end of the drive screw.

6. The surgical instrument according to claim 4, wherein the drive assembly is one of a plurality of drive assemblies disposed radially around the drive connector frame.

7. The surgical instrument according to claim 1, wherein the drive screw extends through an aperture defined through the drive nut.

8. The surgical instrument according to claim 1, wherein the biasing element includes a proximal portion engaged with a distal end of the drive nut and a distal portion disposed within a retention pocket formed in the bore of the housing assembly.

9. The surgical instrument according to claim 8, wherein the biasing element is pre-tensioned to push the drive nut in a proximal direction thereby applying tension to the drive member and preventing the drive member from going slack.

10. The surgical instrument according to claim 1, wherein the end effector includes a jaw assembly and movement of the drive member effectuates a function of the jaw assembly.

11. A surgical instrument for use with a robotic surgical system, the surgical instrument comprising:
- an instrument drive connector including a housing assembly defining a bore therein;
- an elongated shaft having a proximal portion operably coupled to the instrument drive connector and a distal portion having an end effector; and
- a drive assembly housed within the bore of the housing assembly, the drive assembly including:
  - a drive screw rotatable relative to the housing assembly;
  - a drive nut mechanically engaged with the drive screw such that rotation of the drive screw causes longitudinal movement of the drive nut; and
  - a drive member including a rigid proximal end portion secured to the drive nut and a flexible distal end portion in mechanical cooperation with the end effector.

12. The surgical instrument according to claim 11, wherein the proximal end portion of the drive member is a rod, and the distal end portion of the drive member is a cable.

13. The surgical instrument according to claim 11, wherein the drive screw includes a proximal end having an input drive coupler configured to receive rotational forces.

14. The surgical instrument according to claim 11, wherein the drive screw extends through an aperture defined through the drive nut.

15. The surgical instrument according to claim 11, wherein the drive assembly further includes a biasing element surrounding a portion of the drive screw.

16. A robotic surgical system comprising:
- a surgical instrument including:
  - an instrument drive connector including a housing assembly defining a bore therein;
  - an elongated shaft having a proximal portion operably coupled to the instrument drive connector and a distal portion having an end effector; and
  - a drive assembly housed within the bore of the housing assembly, the drive assembly including:
    - a drive screw rotatable relative to the housing assembly;
    - a drive nut mechanically engaged with the drive screw such that rotation of the drive screw causes longitudinal movement of the drive nut;
    - a biasing element surrounding a portion of the drive screw; and
    - a drive member in mechanical cooperation with the drive nut and the end effector.

17. The robotic surgical system according to claim 16, further comprising an instrument drive unit coupled to the instrument drive connector of the surgical instrument.

18. The robotic surgical system according to claim 17, wherein the instrument drive unit includes a motor configured to transfer power and actuation forces to the instrument drive connector.

19. The robotic surgical system according to claim 18, wherein the motor includes an output drive coupler, and the drive screw includes an input drive coupler engaged with the output drive coupler such that rotation of the output drive coupler causes a corresponding rotation of the input drive coupler.

20. The robotic surgical system according to claim 17, further comprising a robotic arm, the instrument drive unit operably coupled to the robotic arm.

* * * * *